United States Patent

Mund et al.

Patent Number: 5,614,246
Date of Patent: Mar. 25, 1997

[54] METHOD FOR MANUFACTURING A SENSOR ELECTRODE

[75] Inventors: Konrad Mund, Uttenreuth; J. Raghavendra Rao, Erlangen; Armin Datz, Poxdorf, all of Germany

[73] Assignee: Pacesetter AB, Solna, Sweden

[21] Appl. No.: 554,767

[22] Filed: Nov. 7, 1995

[30] Foreign Application Priority Data

Nov. 10, 1994 [DE] Germany .................. 44 40 224.4

[51] Int. Cl.⁶ .................. B05D 3/12; B05D 5/12
[52] U.S. Cl. .................. 427/2.24; 427/2.12; 427/386
[58] Field of Search .................. 427/2.24, 386, 427/2.12; 607/122, 123

[56] References Cited

U.S. PATENT DOCUMENTS

| | | | |
|---|---|---|---|
| 3,619,286 | 11/1971 | Gutnajer | 204/290 R |
| 3,721,246 | 3/1973 | Landis | 128/404 |
| 3,964,470 | 6/1976 | Trombley | 623/24 |
| 4,369,104 | 1/1983 | Beckley | 204/290 R |
| 4,611,604 | 9/1986 | Botvidsson et al. | 128/78 |
| 4,737,112 | 4/1988 | Jin et al. | 264/104 |
| 4,773,433 | 9/1988 | Richter et al. | 128/784 |
| 4,784,160 | 11/1988 | Szilagyi | 427/450 |
| 4,853,091 | 8/1989 | Mund et al. | 204/1 T |
| 4,917,760 | 4/1990 | Richter et al. | 156/655 |
| 5,029,585 | 7/1991 | Lieber et al. | 607/125 |
| 5,147,590 | 9/1992 | Preidel et al. | 264/81 |
| 5,235,283 | 8/1993 | Lehne et al. | 324/318 |
| 5,330,520 | 7/1994 | Maddison et al. | 607/122 |
| 5,399,432 | 3/1995 | Schleifstein et al. | 428/403 |
| 5,423,220 | 6/1995 | Finsterwald et al. | 73/642 |
| 5,433,742 | 7/1995 | Willis | 607/122 |

FOREIGN PATENT DOCUMENTS

| | | |
|---|---|---|
| 2345169 | 10/1977 | France . |
| 3313977 | 10/1984 | Germany . |
| WO95/11723 | 5/1995 | WIPO . |

*Primary Examiner*—Diana Dudash
*Attorney, Agent, or Firm*—Hill, Steadman & Simpson

[57] ABSTRACT

In a method for manufacturing a working electrode for an implantable, electrochemical oxygen sensor a thin layer of a uniform mixture composed of an epoxy-based resin, a hardener and powdered vitreous carbon is applied onto a ring or hollow cylinder of biocompatible, inert, electrically conductive material, and the resin is hardened.

13 Claims, No Drawings

METHOD FOR MANUFACTURING A SENSOR ELECTRODE

BACKGROUND OF THE INVENTION

1. Field of the Invention

The invention is directed to a method for manufacturing a working electrode for an implantable, electrochemical oxygen sensors.

2. Description of the Prior Art

In physiologically controlled heart pacemakers, oxygen concentration in the blood or, tissue often serves as a control parameter for adjusting the pacing rate. An implantable, electrochemical oxygen sensor whose working electrode is a vitreous carbon electrode having a smooth surface has proven advantageous for measuring the oxygen concentration (see European Application 0 170 998). For reducing the oxygen dissolved in the electrolyte, this working electrode is placed for a brief time (about 5–50 ms) at a potential of, for example, −1 V (to Ag/AgCl) and then returns to the quiescent potential (approximately 0 volts). It is an advantage that this working electrode need not be provided with a membrane because the vitreous carbon is electro-catalytically inert for the oxidation of substances present in the electrolyte and only catalyzes the oxygen reduction.

An oxygen sensor of the above type has generally been composed of a two-electrode or three-electrode arrangement, with the electrodes assembled in the form of a catheter. The working electrode (of vitreous carbon) is hemispherically fashioned and forms the tip of the catheter. It would be advantageous, however, if the oxygen sensor could be integrated into the electrode cable of a heart pacemaker. For that purpose, however, the working electrode would have to have an annular shape.

SUMMARY OF THE INVENTION it is an object of the present invention to provide a method that allows the manufacture of an annular working electrode for implantable, electrochemical oxygen sensors.

This object is inventively achieved in a method wherein a thin layer of a uniform mixture composed of a resin on an epoxy base, a hardener and powdered vitreous carbon is applied onto a ring or hollow cylinder composed of biocompatible, inert, electrically conductive material, and the resin is cured.

Given the working electrode manufactured according to this method, the effective layer is composed of vitreous carbon power that is embedded into a plastic matrix so that no pores (interstices) are present. The catalytic activity and the electrochemical double-layer capacitance of this layer are low. The layer is also mechanically stable as well as electrically conductive and can be mechanically worked. Vitreous carbon is exposed by a mechanical processing, for example, lathing, this being advantageous for the electrical conductivity. The thickness of the hardened (cured) layer preferably amounts to $\geq 250$ µm. Attempts to fabricate rings or hollow cylinders directly of vitreous carbon led to bodies having an inadequate mechanical stability.

DESCRIPTION OF THE PREFERRED EMBODIMENTS

For manufacturing the working electrode of the invention, the vitreous carbon powder is introduced into the resin in such a concentration that it is assured that the cured, hardened material has an electrical conductivity that is not less than 2 mS/cm. The vitreous carbon content of the mixture of resin, hardener and vitreous carbon preferably amounts to $\geq 50\%$ by weight. The vitreous carbon powder has a grain diameter between 1 and 100 µm, preferably between 10 and 50 µm. Spherical particles have thereby proven especially suitable; however, splintery material can also be utilized. Vitreous carbon, moreover, is a physiologically compatible material.

In the method of the invention, resins on an epoxy base are utilized. These, for example, are standard epoxy resins, particularly bisphenol-based resins. In a known way, epoxy resins are convened into duroplastic plastics with suitable hardeners, i.e. are hardened or cured. This can ensue at room temperature or at an elevated temperature. Suitable hardeners are, in particular, poly-functional aliphatic or aromatic amines and acid anhydrides.

Resins known as EP/IC resins have proven especially suitable, i.e. epoxy/isocyanate-based resins, that are likewise hardened in a known way (see, for example, European Applications 0 129 787 and 0 130 454). Epoxy-based resin plastics, moreover, are biocompatible and biostable, i.e. no dissolving and no degradation ensue in the body.

The rings or hollow cylinders utilized in the method of the invention are composed of biocompatible, inert material. Metals, preferably titanium, platinum and gold, are particularly suited for this purpose. Electrode bodies of titanium can also be advantageously utilized, these being provided with a layer of dense titanium nitride (TiN). Titanium nitride is more conductive than pure titanium, is inert with respect to oxygen and also has good physiological compatibility (see, for example, European Application 0 115 778).

The invention shall be set forth in greater detail with reference to exemplary embodiments.

EXAMPLE 1

15 g of a commercial epoxy resin on the basis of bisphenol A (average molecular weight <700) and 1.5 g of a commercial hardener on the basis of triethylenetetramine are mixed together and degassified 6–8 minutes. 18 g spherical vitreous carbon powder (particle diameter: 20–50 µm) are added to this mixture; mixing is then carefully carried out until a uniform compound is obtained; subsequently, evacuation is carried out for another 20–30 minutes.

The viscous mass is applied onto a titanium ring having a diameter of 2.2 mm and a width of 1.1 mm and is then hardened. The hardening ensues either at room temperature (overnight) or at 80° C. (2 hours). The hardened compound is subsequently mechanically worked, whereby a uniform layer having a thickness of approximately 300 µm is obtained (vitreous carbon content: 52.2%).

EXAMPLE 2

11.6 g of a commercial epoxy resin on the basis of bisphenol A (average molecular weight <350) and 8.4 g diphenylmethanediisocyanate are placed into a 250 ml flask and are degassified for 10 minutes upon agitation at 60° C. Subsequently, 31 g spherical vitreous carbon powder (particle diameter: 20–30/µm) are carefully added and then evacuation is carried out again for 2–3 hours upon agitation at the same temperature. After complete degassification, 0.25 g of a substituted imidazole are added as a hardening catalyst.

The viscous compound is applied onto a titanium ring (diameter: 2.2 mm; width: 1.1 mm) that was previously provided with a thin TiN layer by sputtering; hardening is then carried out at 120° C. (1 hour) and 150° C. (1 hour). The hardened compound is subsequently mechanically worked, whereby a uniform layer having a thickness of approximately 300 µm is obtained (vitreous carbon content: 60.5%).

The electrodes manufactured in the above-described way have a specific electrical impedance in the range between 50 and 150 $\Omega$.cm and have extremely low capacitances of <20 µF/cm$^2$ at a frequency of 1 Hz. These values are comparable to those of electrodes of pure vitreous carbon. Oxygen measurements with electrodes of the invention exhibit a fast and clear response to changes in the oxygen concentration. The sensitivity generally amounts to >12% given a change from 0 to 5% oxygen.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for manufacturing a working electrode for an implantable, electrochemical oxygen sensor, comprising the steps of:

providing an annular element of biocompatible, inert, electrically conductive metal;

providing a layer of a uniform mixture of an epoxy resin, a hardener and powdered vitreous carbon on said annular element; and hardening said resin to produce an annular electrode having a working surface through which current flows which is covered by hardened resin with said vitreous carbon embedded therein.

2. A method as claimed in claim 1 wherein said annular element is in the shape of a ring.

3. A method as claimed in claim 1 wherein said annular element is in the shape of a hollow cylinder.

4. A method as claimed in claim 1 further comprising the additional step of mechanically working a surface of said resin after hardening.

5. A method as claimed in claim 1 wherein the step of applying said layer on said annular element comprises applying a layer of said uniform mixture on said annular element in a thickness for producing a layer after hardening having a thickness of greater than or equal to 250 µm.

6. A method as claimed in claim 1 wherein the step of applying said layer of said uniform mixture comprises applying a layer of said uniform mixture on said annular element for producing a layer after hardening having an electrical conductivity greater than or equal to 2 mS/cm.

7. A method as claimed in claim 1 wherein the step of applying said thin layer of said uniform mixture comprises applying a layer of a uniform mixture having a vitreous carbon content greater than or equal to 50% by weight.

8. A method as claimed in claim 1 wherein the step of applying a layer of said uniform mixture comprises applying said layer of said uniform mixture containing vitreous carbon powder having a grain size between 1 and 100 micrometers.

9. A method as claimed in claim 1 wherein the step of applying a layer of said uniform mixture comprises applying said layer of said uniform mixture containing vitreous carbon powder having a grain size between 10 and 50 micrometers.

10. A method as claimed in claim 1 wherein the step of applying said layer of said uniform mixture comprises applying a layer of a uniform mixture composed of an epoxy/isocyanate resin, a hardener and powered vitreous carbon.

11. A method as claimed in claim 1 further comprising the additional step of selecting said metal from the group consisting of titanium, platinum and gold.

12. A method for manufacturing a working electrode for an implantable, electrochemical oxygen sensor, comprising the steps of:

providing an annular biocompatible, inert, electrically conductive element composed of titanium coated with titanium nitride;

providing a layer of a uniform mixture of an epoxy resin, a hardener and powdered vitreous carbon on said annular element; and hardening said resin to produce an annular electrode having a working surface through which current flows which is covered by hardened resin with said vitreous carbon embedded therein.

13. A method for manufacturing a working electrode for an implantable, electrochemical oxygen sensor, comprising the steps of:

providing an annular element of biocompatible, inert, electrically conductive material;

providing a layer of a uniform mixture of an epoxy resin, a hardener and powdered vitreous carbon on said annular element; and hardening said resin to produce an annular electrode having a working surface through which current flows which is covered by hardened resin with said vitreous carbon embedded therein, said layer after hardening having a thickness of greater than or equal to 250 µm.

* * * * *